United States Patent [19]

Nikoonahad et al.

[11] Patent Number: 5,883,710
[45] Date of Patent: Mar. 16, 1999

[54] SCANNING SYSTEM FOR INSPECTING ANOMALIES ON SURFACES

[75] Inventors: Mehrdad Nikoonahad, Menlo Park; Stanley E. Stokowski, Danville, both of Calif.

[73] Assignee: Kla-Tencor Corporation, San Jose, Calif.

[21] Appl. No.: 499,995

[22] Filed: Jul. 10, 1995

Related U.S. Application Data

[63] Continuation-in-part of Ser. No. 351,664, Dec. 8, 1994.
[51] Int. Cl.$^6$ .................................................. G01N 21/00
[52] U.S. Cl. ............................................................ 356/237.2
[58] Field of Search ...................... 356/243, 237, 356/394, 338, 398, 335–343, 445–448, 73, 369, 237.1, 237.6, 238.1–238.3, 239.1–239.8, 243.1–243.8; 250/559.01, 559.09, 559.16

[56] References Cited

U.S. PATENT DOCUMENTS

| | | |
|---|---|---|
| 3,851,951 | 12/1974 | Eveleth . |
| 4,391,524 | 7/1983 | Steigmeier et al. . |
| 4,405,238 | 9/1983 | Grobman et al. . |
| 4,441,124 | 4/1984 | Heebner et al. . |
| 4,556,290 | 12/1985 | Roulot . |
| 4,589,773 | 5/1986 | Ido et al. . |
| 4,601,576 | 7/1986 | Galbraith . |
| 4,614,427 | 9/1986 | Koizumi et al. . |
| 4,650,983 | 3/1917 | Suwa . |
| 4,728,190 | 3/1988 | Knollenberg . |
| 4,748,333 | 5/1988 | Mizutani et al. . |
| 4,844,617 | 7/1989 | Kelderman et al. . |
| 4,864,123 | 9/1989 | Mizutani et al. . |
| 4,889,998 | 12/1989 | Hayano et al. . |
| 4,898,471 | 2/1990 | Stonestrom et al. . |
| 4,912,487 | 3/1990 | Porter et al. . |
| 4,966,457 | 10/1990 | Hayano et al. . |
| 5,122,898 | 6/1992 | Picault . |
| 5,166,516 | 11/1992 | Kajimura . |
| 5,272,517 | 12/1993 | Tokura . |
| 5,274,434 | 12/1993 | Morioka et al. ......................... 356/237 |
| 5,317,380 | 5/1994 | Allemand . |
| 5,436,464 | 7/1995 | Hayano et al. ......................... 356/237 |
| 5,576,831 | 11/1996 | Nikoonahad et al. .................. 356/237 |

OTHER PUBLICATIONS

Gottlieb, "Acoustooptic Scanners and Modulators", publication of Westinghouse ELectric Corportion, pp. 615–685.

Alumont et al., "Dual sensor technology for high–speed detectionof 0.1 micron defects", SPIE vol. 1926 Integrated Circuit Motrology, Inspection, and Process Control VII, 1993, pp. 1–12.

Nikoonhad et al, "New Laser Scanning Techniques for Wafer Inspection", SPIE vol. 26 38, Feb. 1995, pp. 285–301.

Dralla et al "Inspection . . . Beyond"; presented at Semicon Kansai Japan Jun. 15–17, 1994.

Clark et al "Dynamic Performance . . . Inspection" J. Vac. Sci. Technol. B (107 (6) Nov./Dec. 1992 pp. 2638–2642.

Primary Examiner—K P Hantis
Attorney, Agent, or Firm—Majestic, Parsons, Siebert & Hsue P.C.

[57] ABSTRACT

A high sensitivity and high throughput surface inspection system directs a focused beam of light at a grazing angle towards the surface to be inspected. Relative motion is caused between the beam and the surface so that the beam scans a scan path covering substantially the entire surface and light scattered along the path is collected for detecting anamolies. The scan path comprises a plurality of arrays of straight scan path segments. The focused beam of light illuminates an area of the surface between 5–15 microns in width and this system is capable of inspecting in excess of about 40 wafers per hour for 150 millimeter diameter wafers (6-inch wafers), in excess of about 20 wafers per hour for 200 millimeter diameter wafers (8-inch wafers) and in excess of about 10 wafers per hour for 300 millimeter diameter wafers (12-inch wafers).

46 Claims, 6 Drawing Sheets

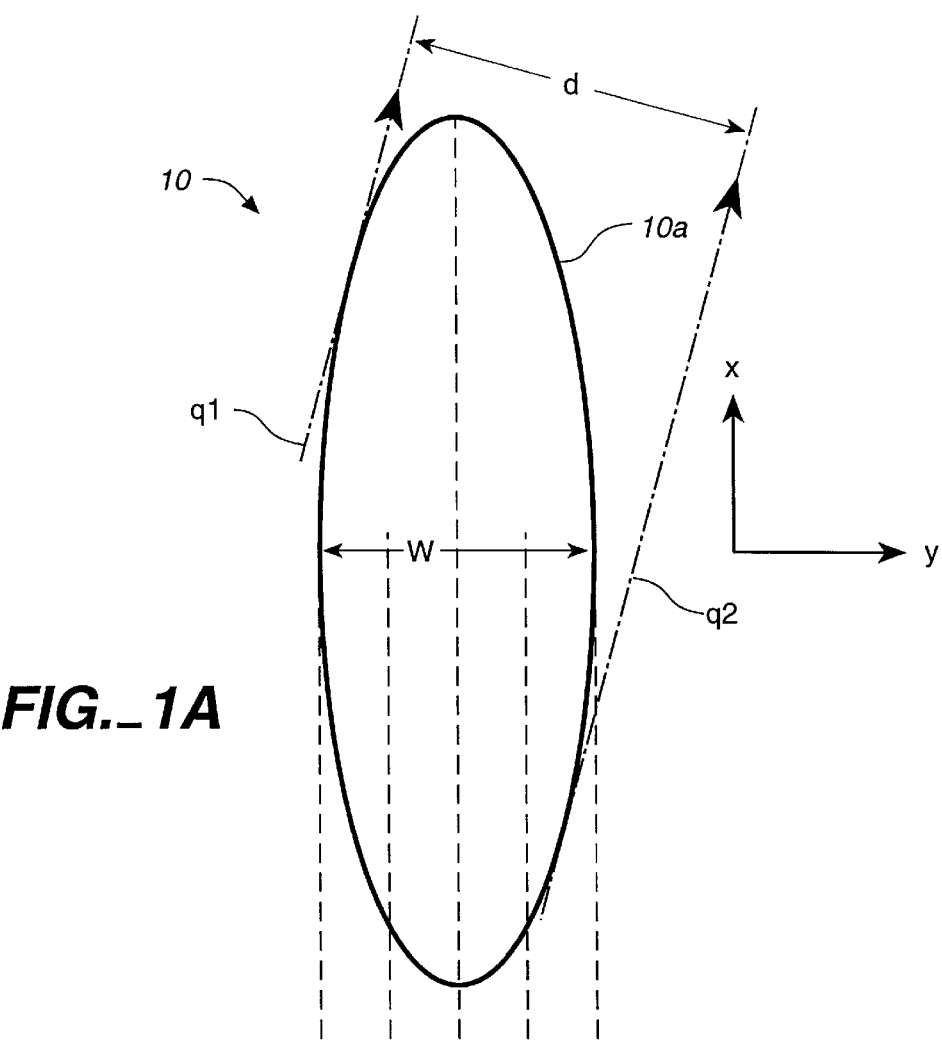
FIG._1A
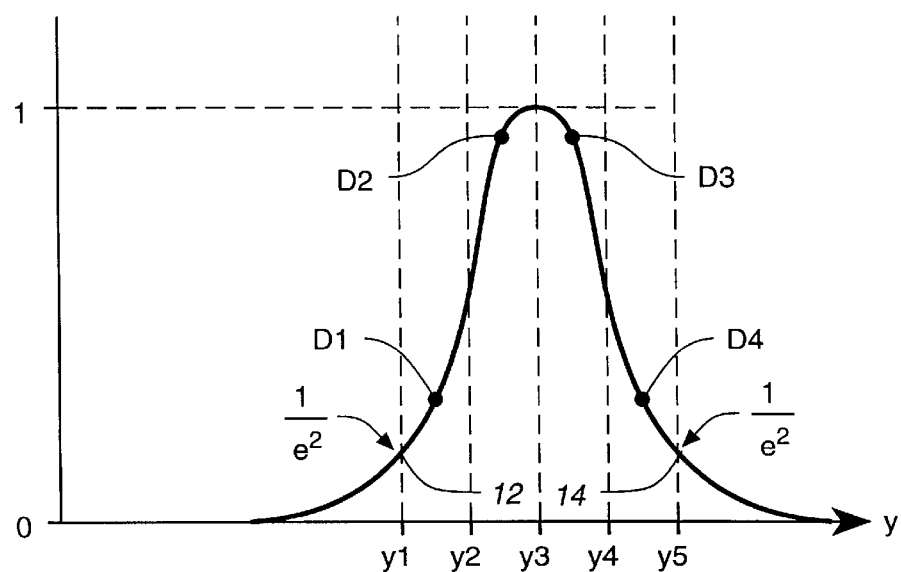
FIG._1B

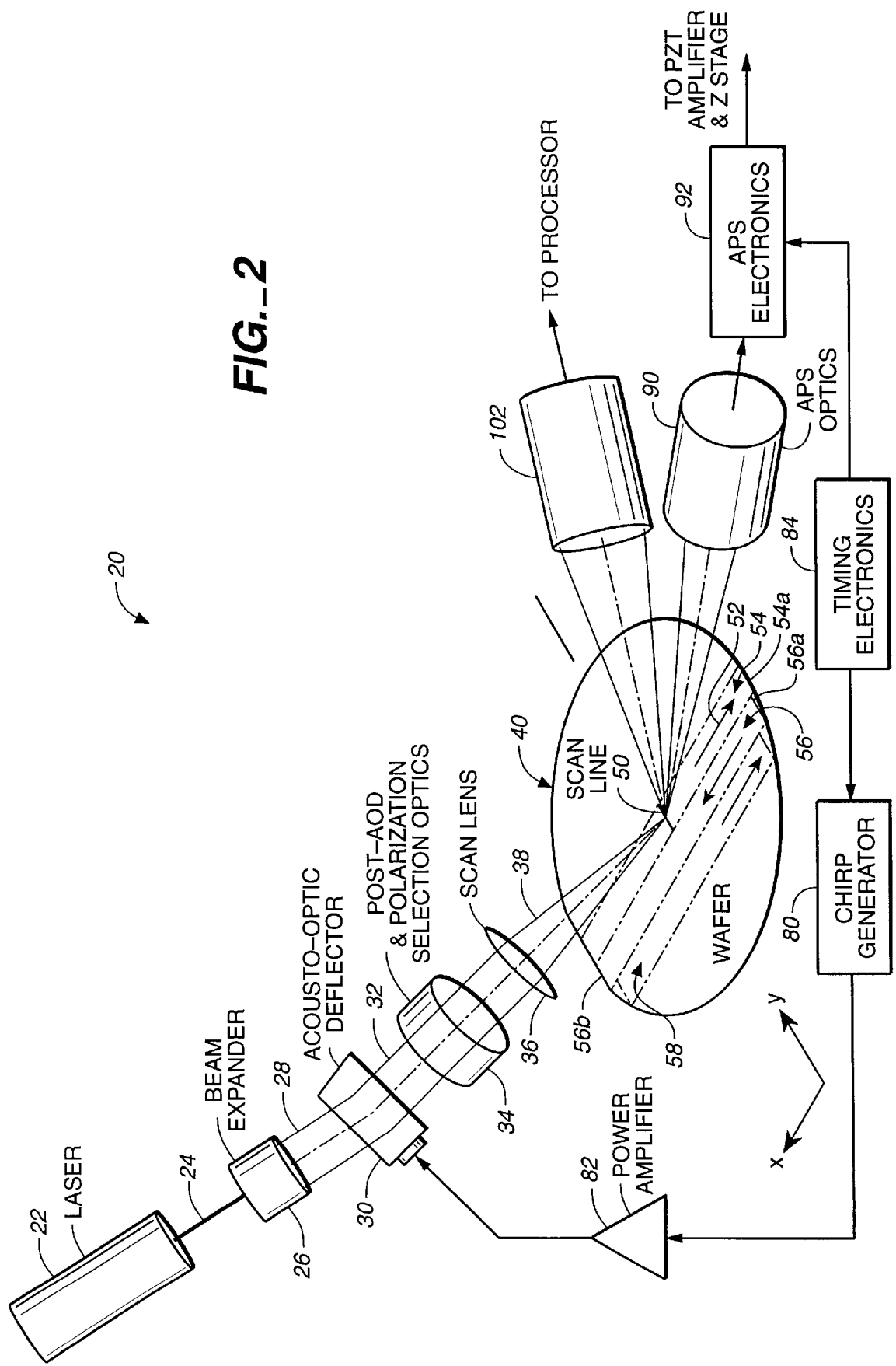
FIG._2

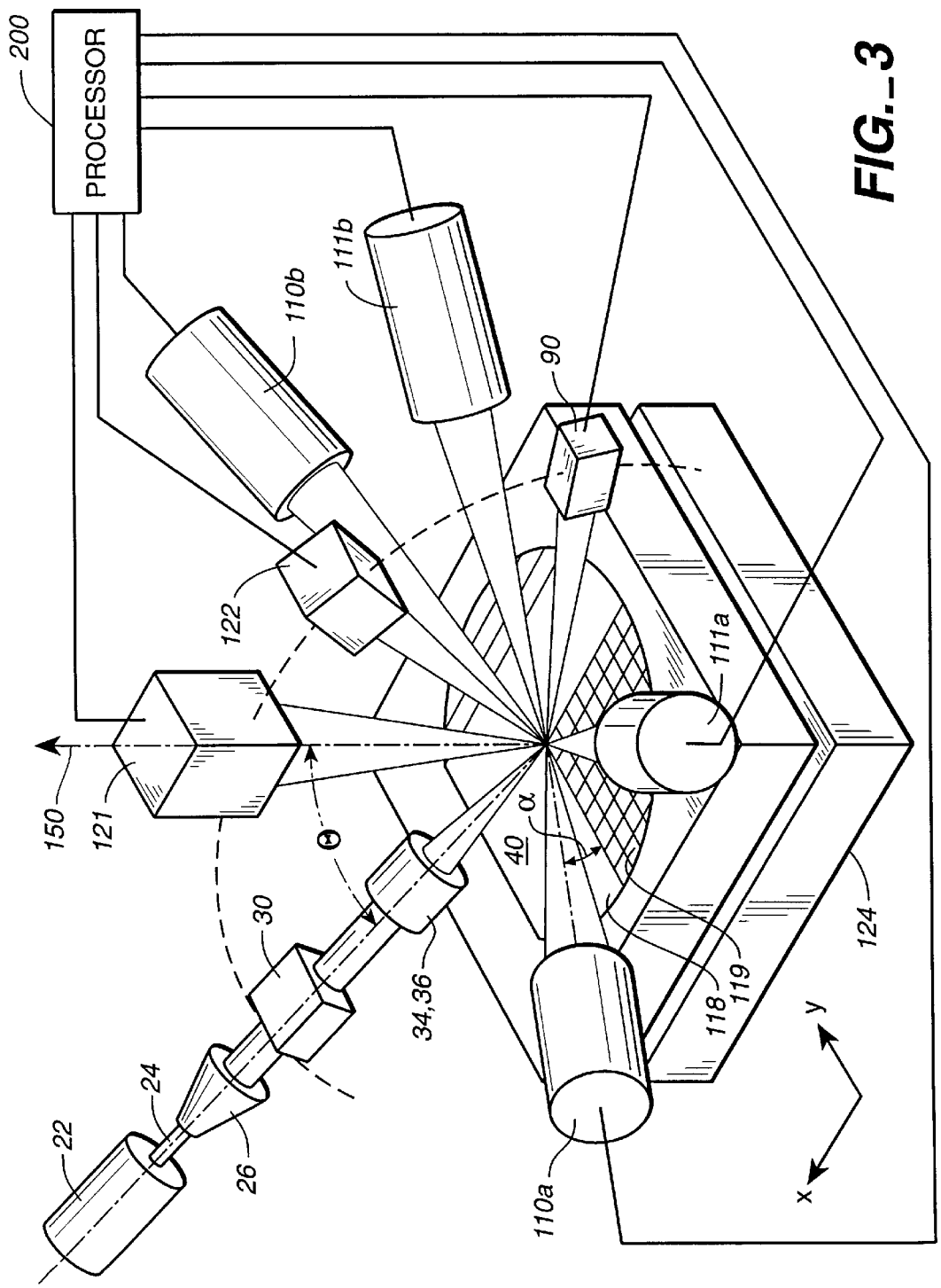
FIG._3

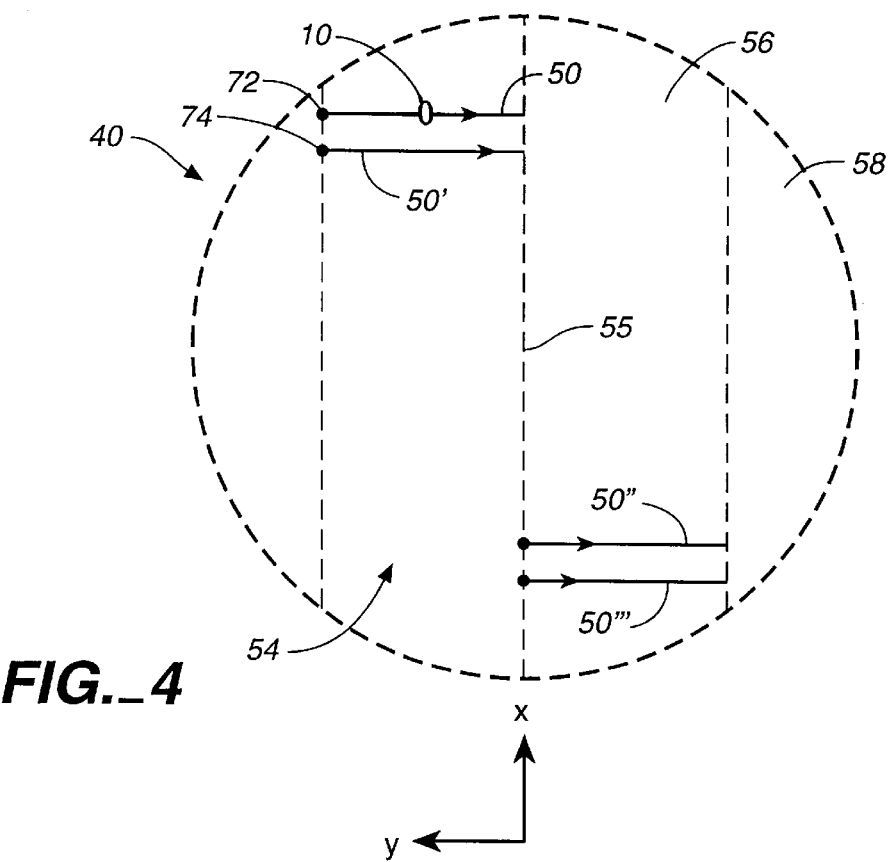
FIG._4
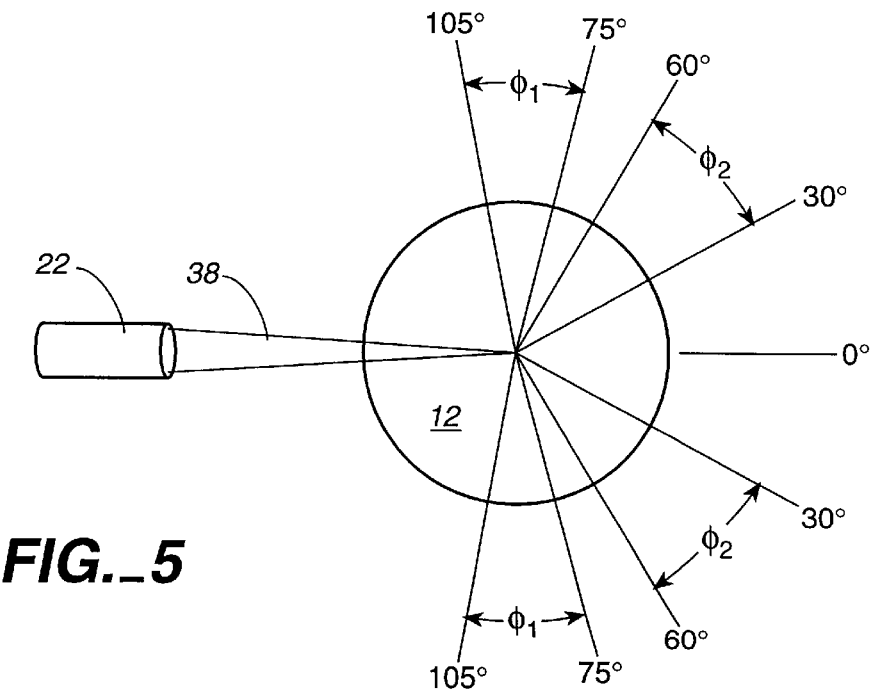
FIG._5

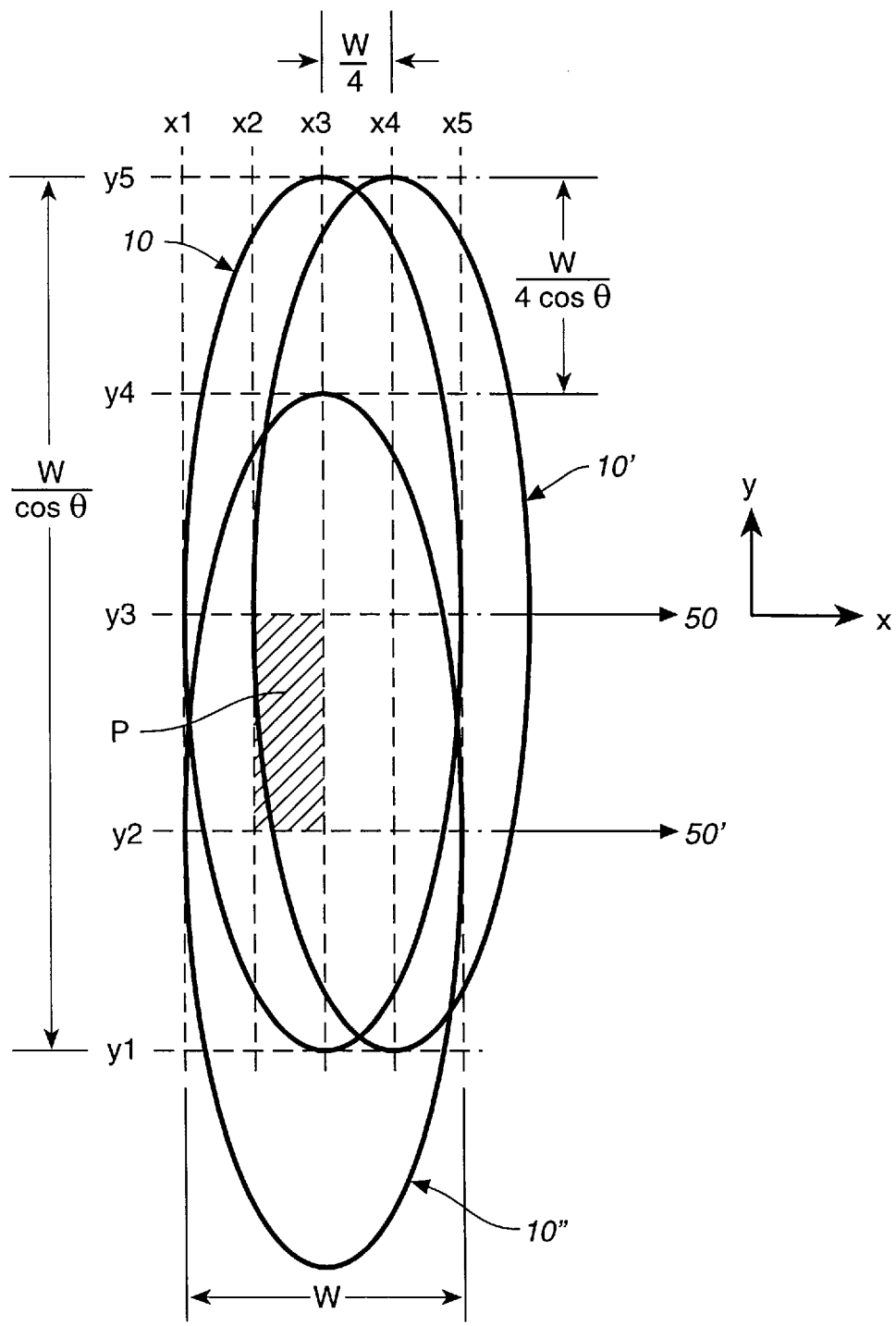
FIG._6

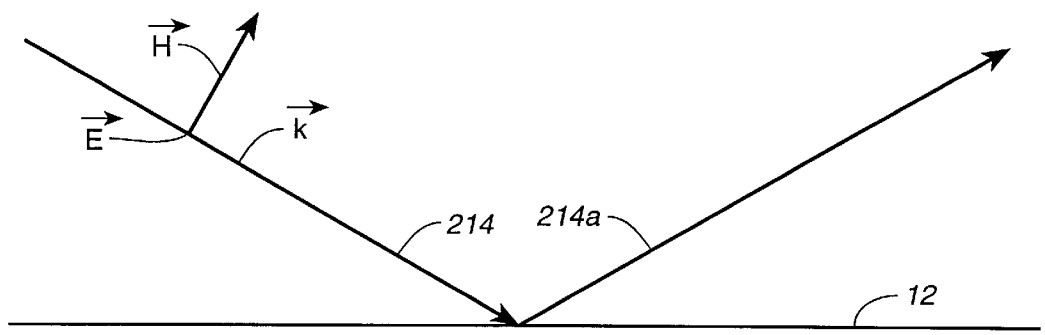
FIG._7A
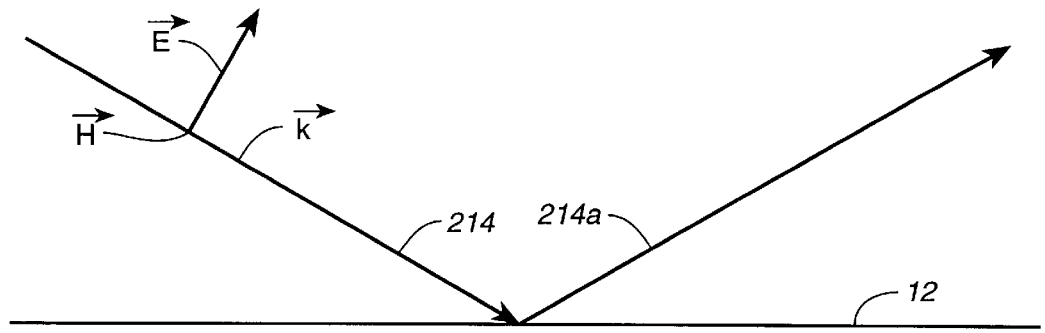
FIG._7B

SCANNING SYSTEM FOR INSPECTING ANOMALIES ON SURFACES

CROSS-REFERENCE TO RELATED APPLICATIONS

This application is a continuation-in-part application of parent application entitled "Optical Scanning System for Surface Inspection," by Mehrdad Nikoonahad, Keith D. Wells, and Brian C. Leslie, Ser. No. 08/351,664 filed Dec. 8, 1994. This application is also related to the patent application entitled "Optical Wafer Positioning System," by Mehrdad Nikoonahad, Philip R. Rigg, Keith D. Wells, and David S. Calhoun, Ser. No. 08/361,131 filed Dec. 21, 1994 ("Related Application"). Both prior applications are incorporated by reference herein in their entirety.

BACKGROUND OF THE INVENTION

This invention relates in general to surface inspection systems, and in particular, to a high speed scanner system for inspecting anamolies on surfaces such as semiconductor wafers, photomasks, reticles, ceramic tiles, and other surfaces.

The size of semiconductor devices fabricated on silicon wafers has been continually reduced. At the time this application is filed, for example, semiconductor devices can be fabricated at a resolution of a half micron or less and sixty-four (64) megabyte DRAMs are being fabricated with 0.35 micron design rule. The shrinking of semiconductor devices to smaller and smaller sizes has imposed a much more stringent requirement for sensitivity of wafer inspection instruments which are called upon to detect contaminant particles and pattern defects that are small compared to the size of the semiconductor devices. On the other hand, it is desirable for wafer inspection systems to provide an adequate throughput so that these systems can be used in production runs to detect defective wafers.

In U.S. Pat. No. 4,898,471 to Stonestrom et al. assigned to the present assignee of this application, the area illuminated on a wafer surface by a scanning beam is an ellipse which moves in the scan direction. In one example given by Stonestrom et al., the ellipse has a width of 20 microns and a length of 115 microns. Light scattered by anamolies or patterns in such illuminated area is detected by photodetectors placed at azimuthal angles in the range of 80° to 100°. The signals detected by the photodetectors are used to construct templates. When the elliptical spot is moved in the scan direction to a neighboring position, scattered light from structures within the spot is again detected and the photodetector signal is then compared to the template to ascertain the presence of contaminant particles or pattern defects as opposed to regular pattern. In Stonestrom et al., the scanning beam scans across the entire wafer to illuminate and inspect a long narrow strip of the wafer extending across the entire dimension of the wafer in the scanning direction. The wafer is then moved by a mechanical stage in a direction perpendicular to the scanning direction for scanning a neighboring elongated strip. This operation is then repeated until the entire wafer is covered.

While the system of Stonestrom et al. performs well for inspecting wafers having semiconductor devices that are fabricated with coarser resolution, with the continual shrinking of the size of the devices fabricated, it is now desirable to provide an improved inspection tool that can be used to detect very small size anamolies that may be difficult to detect using Stonestrom et al.'s system.

SUMMARY OF THE INVENTION

This invention is based on the recognition that very small anamolies can be detected by reducing the size of the area that is illuminated by the scanning light beam. Light scattered from structures in the spot will include background, such as light scattered by pattern on the surface, as well as light that is scattered by anomalies such as contaminant particles, pattern defects or imperfections of the surface. Such background can have a significant amplitude. For this reason, if the anamoly is of a size which is small compared to the size of the illuminated area, the scattered light from such anamoly may be overwhelmed by and become undetectable from the background. By reducing the size of the illuminated area or spot size, the ratio of the light intensity scattered by an anomaly to that of the background will be increased, thereby increasing detection sensitivity. However, with a smaller spot size, it will be more difficult to maintain the uniformity of the spot along a long straight scan line across the entire wafer. By breaking up the scan path into short segments, it is possible to employ a smaller spot size while at the same time maintaining uniformity of the spot along the path. From the system point of view, by reducing the length of the scan, the size of the collection optics for detecting forward scattered light becomes more manageable.

Thus one aspect of the invention is directed towards a method for detecting anamolies on a surface, comprising the steps of directing a beam of light at a grazing angle towards the surface, causing relative motion between the beam and the surface so that the beam scans a scan path covering substantially the entire surface; and collecting light scattered along said path for detecting anamolies. The scan path includes a plurality of arrays of scan path segments, wherein each of at least some of such scan path segments has a span shorter than the dimensions of the surface.

As used in this application, "minimum width" of the illuminated area or spot on the surface to be inspected is defined as the minimum dimension of a boundary around the area or spot along any direction on the surface, where the boundary is defined as the locations on the surface where the illumination light intensity is a predetermined fraction or percentage of the maximum intensity of illumination in the area or spot. In the description of the preferred embodiment, for example, the boundary is where the light illumination intensity is $1/e^2$ of the maximum intensity of illumination in the area or spot, e being the natural number. The minimum dimension is the minimum distance between two parallel lines that enclose between them the boundary of the area or spot. The term "minimum width" is explained in more detail below.

Another consideration of the invention is to provide an adequate throughput while data is collected at a moderate rate for defect detection so that the data collection and processing system employed need not be overly complex and expensive.

Thus another aspect of the invention is directed towards a method for detecting anamolies on the surface of a semiconductor wafer, comprising directing a beam of light towards a surface to illuminate an area of the surface defining a spot having a spot size whose minimum width is in the range of about 5 to 15 microns, causing relative motion between the beam and the wafer so that the beam scans a path covering the entire surface; and collecting light scattered along said path for detecting anamolies. The spot size and the directing and causing steps are such that the beam scanning substantially inspects the entire surface of the wafer at a throughput in excess of about 40 wafers per hour for 150 millimeter diameter wafers, at a throughput in excess of about 20 wafers per hour for 200 millimeter diameter wafers, and at a throughput in excess of about 10 wafers per hour for 300 millimeter diameter wafers.

Yet another aspect of the invention is directed towards a method for detecting anamolies on a surface, comprising the steps of directing a beam of light towards the surface to illuminate an area of the surface defining a spot having a spot size whose minimum width is in the range of about 5 to 15 microns, causing relative motion between the beam and the surface so that the beam scans a path covering substantially the entire surface; and collecting light scattered along said path for detecting anamolies. The spot size and said directing and causing steps are such that the surface is inspected at a speed not less than about 1.5 $cm^2/s$.

Still another aspect of the invention is directed towards a method for detecting anamolies on a surface, comprising the steps of directing a beam of light towards said surface to illuminate an area of the surface defining a spot having a spot size whose minimum width is in the range of about 5 to 15 microns, causing relative motion between the beam and the surface so that the beam scans a path covering substantially the entire surface; and collecting light scattered along said path for detecting anamolies. The surface has dimensions of not less than 200 millimeters in any direction along the surface. The directing and causing steps are such that the beam scans substantially the entire surface in about 50 to 90 seconds.

Another aspect of the invention is directed towards a system for detecting anamolies on a surface, comprising means for directing a beam of light at a grazing angle toward said surface; means for causing relative motion between the beam and the surface so that the beam scans a scan path covering substantially the entire surface; and means for collecting light scattered along said path for detecting anamolies. The scan path includes a plurality of arrays of scan path segments, wherein each of at least some of such scan path segments has a span shorter than the dimensions of the surface.

One more aspect of the invention is directed towards a system for detecting anamolies on a surface of a semiconductor wafer, comprising means for directing a beam of light towards said surface to illuminate an area of the surface defining a spot having a spot size whose minimum width is in the range of about 5 to 15 microns; means for causing relative motion between the beam and the wafer so that the beam scans a path covering substantially the entire surface; and means for collecting light scattered along said path for detecting anamolies. The spot size and said directing and causing means are such that the beam scanning substantially inspects the entire surface of the wafer at a throughput in excess of about 40 wafers per hour for 150 millimeter diameter wafers, at a throughput in excess of about 20 wafers per hour for 200 millimeter diameter wafers, and at a throughput in excess of about 10 wafers per hour for 300 millimeter diameter wafers.

Yet another aspect of the invention is directed towards a system for detecting anamolies on a surface, comprising means for directing a beam of light toward said surface to illuminate an area of the surface defining a spot having a spot size whose minimum width is in the range of about 5 to 15 microns; means for causing relative motion between the beam and the surface so that the beam scans a path covering substantially the entire surface; and means for collecting light scattered along said path for detecting anamolies. The spot size and said directing and causing means are such that the surface is inspected at a speed not less than about 1.5 $cm^2/s$.

Still one more aspect of the invention is directed towards a system for detecting anamolies on a surface, comprising means for directing a beam of light toward said surface to illuminate an area of the surface defining a spot having a spot size whose minimum width is in the range of about 5 to 15 microns; means for causing relative motion between the beam and the surface so that the beam scans a path covering substantially the entire surface; and means for collecting light scattered along said path for detecting anamolies. The surface has dimensions of not less than 200 millimeters in any direction along the surface. The directing and causing means are such that the beam scans substantially the entire surface in about 50 to 90 seconds.

BRIEF DESCRIPTION OF THE DRAWINGS

FIG. 1A is a schematic view of an elliptical-shaped illuminated area or spot on a surface to be inspected to illustrate the invention.

FIG. 1B is a graphical illustration of the illumination intensity across the width or short axis of the elliptical spot of FIG. 1A for defining a boundary of the spot and to illustrate the invention.

FIG. 2 show partially in perspective and partially in block diagram form a system for inspecting anamolies of a semiconductor wafer surface to illustrate the preferred embodiment of the invention.

FIG. 3 is a perspective view showing in more detail the illumination and collection features of the system of FIG. 2.

FIG. 4 is a schematic view of a small portion of a semiconductor wafer surface illustrating the scan path of an illumination spot on the surface to illustrate the preferred embodiment.

FIG. 5 is a schematic view illustrating the illumination and collection angles of the system of FIG. 3.

FIG. 6 is a schematic view of three elliptical illuminated areas or spots to illustrate the scanning and data acquisition processes of this invention.

FIGS. 7A, 7B are side views illustrating two different polarization schemes employed by present invention for illuminating a surface to be inspected.

For simplicity, identical components in the different figures of this invention are labeled by the same numerals.

DETAILED DESCRIPTION OF THE PREFERRED EMBODIMENT

FIG. 1A is a schematic view of an elliptical-shaped illuminated area (or spot) of a surface inspected by the system of this invention to illustrate the invention. As explained below, the laser beam illuminating the surface inspected approach the surface at a grazing angle, so that even though the illumination beam has a generally circular cross-section, the area illuminated is elliptical in shape such as area 10 in FIG. 1A. As known to those skilled in the art, in light beams such as laser beams, the intensity of the light typically does not have a flat distribution and does not fall off abruptly to zero across the boundary of the spot illuminated, such as at boundary 10a of spot 10 of FIG. 1A. Instead, the intensity falls off at the outer edge of the illuminated spot at a certain inclined slope, so that instead of sharp boundaries such as boundary 10a illustrated in FIG. 1A, the boundary is typically blurred and forms a band of decreasing intensity at increasing distance away from the center of the illuminated area.

In many lasers, the laser beam produced has a Gaussian intensity distribution, such as that shown in FIG. 1B. FIG. 1B is a graphical illustration of the spatial distribution of the illumination intensity in the Y direction of a laser beam that is used in the preferred embodiment to illuminate spot 10 of a surface to be inspected as shown in FIG. 1A, and thus is also the illumination intensity distribution across spot 10 in the Y direction. As shown in FIG. 1B, the illumination intensity has been normalized so that the peak intensity is 1, and the illumination intensity has a Gaussian distribution in the Y direction as well as in the X direction. Points 12 and 14 are at spatial locations y1 and y5 at which points the illumination intensity drops to $1/e^2$ of the peak intensity, where e is the natural number. AS used herein to describe the preferred embodiment, the minimum width of spot 10 is the distance between these two points (distance between y1 and y5) is the length of the short axis of elliptical illuminated area 10 and denoted as the width w in FIG. 1A. The spot 10 is defined by the area within a boundary 10a where the illumination is $1/e^2$ of that of the maximum intensity of illumination at the center of the spot.

As a broader definition, "minimum width" of the elliptical spot 10a may be defined as the minimum distance between two parallel lines that enclose between them the boundary of the area or spot. In reference to spot 10 in FIG. 1A, for example, if one were to draw two parallel lines enclosing the boundary 10a, such as lines q1, q2, the distance between lines q1, q2 is d, which is minimized when both q1, q2 touch the boundary 10a. The distance d is minimum for all directions of q1, q2 when the lines q1, q2 coincide with grid lines y1, y5, so that the minimum width of the spot 10 is w. Even where 10a is not an ellipse, but is of another shape such as rectangular, square, or irregular in shape, the same broader definition is applicable.

FIG. 1B shows only the main lobe of the laser or light beam. It is known that the main lobe is also accompanied by sidelobes, so that areas of the surface outside of area or spot 10 would also be illuminated; scattering by structures of the surface of the light in the sidelobes and collected by the detectors causes noise.

In the description above, it is indicated that for a spot which is relatively small compared to the size of the surface to be inspected, it will be difficult to maintain uniformity of the spot across a scan line which spans the entire length or width of the wafer. In reference to FIGS. 1A, 1B, variation in the minimum width (as defined above) w of the main lobe of the focal plane intensity distribution, and the level of the sidelobes is a measure of the uniformity of the spot 10 as the beam scans across the surface. Where the minimum width and the sidelobes level vary little over the scan line, the spot is said to be uniform. In other words, when the spot size is relatively small compared to the size of the surface to be inspected, it will be difficult to maintain uniform width of the main lobe and uniform level of the sidelobes of the focal plane intensity distribution throughout the extent of a long scan line across the entire width of the wafer. A variation in either one of these two parameters (width of main lobe and sidelobe level) leads to a variation in detection sensitivity along the scan direction which is undesirable.

In view of the above problems, Applicants have invented a surface inspection system where the size of the area illuminated by the scanning light beam can be reduced while maintaining uniform detection sensitivity by causing the scanning light beam to scan short scan path segments having a spatial span less than the dimension of the surface it is scanning, as illustrated in the preferred embodiment in FIGS. 2 and 4, where these short scan path segments are not connected together but are located so that they form arrays of scan path segments as illustrated in more detail below.

The surface inspection system of this invention will now be described in reference to FIGS. 2 and 3. As shown in FIG. 2, system 20 includes a laser 22 providing a laser beam 24. Beam 24 is expanded by beam expander 26 and the expanded beam 28 is deflected by acousto-optic deflector (AOD) 30 into a defected beam 32. The deflected beam 32 is passed through post-AOD and polarization selection optics 34 and the resulting beam is focused by telecentric scan lens 36 onto a spot 10 on surface 40 to be inspected, such as that of a semiconductor wafer, photomask or ceramic tile, patterned or unpatterned.

In order to move the illuminated area that is focused onto surface 40 for scanning the entire surface, the AOD 30 causes the deflected beam 32 to change in direction, thereby causing the illuminated spot 10 on surface 40 to be scanned along a scan line 50. As shown in FIG. 2, scan line 50 is preferably a straight line having a length which is smaller than the dimension of surface 40 along the same direction as the scan line. Even where line 50 is curved, its span is less than the dimension of surface 40 along the same general direction. After the illuminated spot has completed scanning surface 40 along scan line 50, surface 40 of the wafer is moved along the X axis so that the illuminated area of the surface moves along arrow 52 and AOD 30 causes the illuminated spot to scan along a scan line parallel to scan line 50 and in adjacent position spaced apart from scan line 50 along the negative X axis. After the illuminated spot has covered such scan line, surface 40 is moved by a small distance so that the area of the surface to be illuminated is moved along direction 52 in order to scan an adjacent scan line at a different x position. As described below, this small distance preferably is equal to about one quarter of the height of spot 10. This process is repeated until the illuminated spot has covered strip 54; at this point in time the illuminated area is at or close to the edge 54a. At such point, the surface 40 is moved along the Y direction by about the length of scan line 50 in order to scan and cover an adjacent strip 56, beginning at a position at or close to edge 56a. The surface in strip 56 is then covered by short scan lines such as 50 in a similar manner until the other end or edge 56b of strip 56 is reached at which point surface 50 is again moved along the Y direction for scanning strip 58. This process is repeated prior to the scanning of strip 54, 56, 58 and continues after the scanning of such strips until the entire surface 40 is scanned. Surface 40 is therefore scanned by scanning a plurality of arrays of short path segments the totality of which would cover substantially the entire surface 40.

FIG. 4 is an exploded view of a portion of the two strips 54, 56 and smaller portions of two other neighboring strips to illustrate in more detail the above-described scanning process. In the preferred embodiment as shown in FIG. 4, the optical beam 38 scans in only one direction as illustrated by the arrows of scan path segments 50, 50', 50", 50'". Scan path 50 has an effective start location at 72 and spot 10 moves to the right therefrom until it reaches the border 55 between strips 54 and 56. Upon reaching border 55, a stage (see FIG. 3) moves the surface 40 in the X direction perpendicular to the scanning direction Y and the spot assumes the new start position 74 and moves along a scan line 50' parallel to scan line 50. The movement of the spot 10 along scan lines 50, 50', 50", 50'" and so on is achieved by means of AOD 30 as explained below.

The deflection of beam 32 by AOD 30 is controlled by chirp generator 80 which generates a chirp signal. The chirp signal is amplified by amplifier 82 and applied to the transducer portion of AOD 30 for generating sound waves to cause deflection of beam 32 in a manner known to those skilled in the art. For a detailed description of the operation of the AOD, see "*Acousto optic Scanners and Modulators,*" by Milton Gottlieb in *Optical Scanning,* ed. by Gerald F. Marshall, Dekker 1991, pp. 615–685. Briefly, the sound waves generated by the transducer portion of AOD 30 modulates the optical refractive index of an acoustooptic crystal in a periodic fashion thereby leading to deflection of beam 32. Chirp generator 80 generates appropriate signals so that after being focused by lens 36, the deflection of beam 32 causes the focused beam to scan along a scan line such as line 50 in the manner described.

Chirp generator 80 is controlled by timing electronic circuit 84 which in the preferred embodiment includes includes a microprocessor. The microprocessor supplies the beginning and end frequencies f1, f2 to the chirp generator 80 for generating appropriate chirp signals to cause the deflection of beam 32 within a predetermined range of deflection angles determined by the frequencies f1, f2. The auto-position sensor (APS) optics 90 and APS electronics 92 are used to detect the level or height of surface 40 and form a part of the Related Application. Detectors such as detector 111$b$ collects light scattered by anamolies as well as the surface and other structures thereon along scan line 50 and provides output signals to a processor in order to detect and analyze the characteristics of the anamolies.

FIG. 3 is a perspective view of system 20 of FIG. 2 showing in more detail the arrangement of the collection or detection channels to illustrated the preferred embodiment. As shown in FIG. 3, four collection channels are used, two channels 110$a$, 110$b$ for collecting scattered light that is within the respective ranges of azimuthal angles of $-(75°-105)°$ and $(75°-105)°$. Two additional collection channels 111$a$, 111$b$ are also employed for detecting forward scattered light that is within the respective ranges of azimuthal angles of $-(30-60)°$ and $(30-60)°$. If desired, it is of course possible to employ four independent collection channels with other different solid angles of collection, two of said collection channels located in the forward direction to collect light in the forward direction centered substantially at $\pm 45°$ azimuthally and two of the channels are located to collect light centered substantially at $\pm 90°$ azimuthally.

FIG. 5 is a top view of the angles of collection of the four detectors. As shown in FIG. 5, the solid angles of collection of channels 110$a$, 110$b$ are labeled $\Phi_1$ and those for channels 111$a$, 111$b$ are labeled $\Phi_2$. To simplify the drawing, the components between laser 22 and focus beam 38 are not shown in FIG. 5. In reference to FIG. 3, system 20 also includes an imaging channel 121 and an alignment/registration channel 122.

Surface 40 may be smooth (118) or patterned (119). The incident focus beam 38 is preferably in the range of about 10°–85° to the normal direction 150 to the surface 40 and more preferably within the range of 50°–80° from the normal; in FIG. 3, this angle is labelled θ. The four channels of collection are preferably at elevation angles α that will collect scattered light from 3°–30° from the plane of surface 40.

Improved Sensitivity of Detection

From the point of view of sensitivity of detection, it is desirable to design the illumination optics portion of system 20 so that the minimum width w of the illuminated spot 10 is minimized. The minimum width w is proportional to the focal length of lens 36 and inversely proportional to the beam diameter of beam 28 and 32. Therefore, the minimum width w can be reduced by reducing the focal length of lens 36 or increasing diameter of beam 28, or both. If the focal length of lens 36 is increased, however, this will increase the length of scan line 50 which may be undesirable. If the diameter of beam 28 becomes comparable to the clear aperture of the crystal in AOD 30, this will produce higher level sidelobes which is undesirable. As noted above, increased level of sidelobes will increase background signal level. Applicants discovered that it is preferable for the ratio k between the clear aperture of the crystal in the AOD 30 to diameter of beam 28 and 32 to exceed 1.2.

It is possible to increase the beam diameter of beam 28 and 32 by employing a long AOD crystal, while maintaining k to be above 1.2. However, in addition to cost considerations, a larger AOD crystal will cause larger losses, thereby degrading the diffraction efficiency of the AOD device. For this reason, it is desirable to employ AOD crystals that are as small as possible, while at the same time meeting the sensitivity and throughput requirements. Assuming that the beam 28 that is entering the AOD 30 has a Gaussian intensity profile, the clear aperture of the AOD, D, satisfies:

$$D = 4\mathrm{klv}/\pi w \Delta f, \tag{1}$$

where $\pi$ is the ratio of the circumference of a circle to its diameter.

Where 1 is the scan line of scan path segment 50, v is the acoustic velocity in the AOD crystal 30, w is the length of the short axis of the elliptical spot (or the minimum width of the spot if not elliptical) on surface 40, $\Delta$ or (f2–f1) is the bandwidth of the AOD 30. The constant k is preferably in the range 1.2–5. In one embodiment, k is 1.7 and 1 is in the range of about 2–10 millimeters.

Throughput Considerations

For a semiconductor wafer inspection instrument to be used for wafer inspection in actual production for inspecting the entire surface of the wafer, throughput considerations are paramount. Therefore, in addition to sensitivity capability described above, it is also desirable for the wafer inspection system of this invention to have a high throughput. The time required for inspecting semiconductor wafers first includes the time required for the illuminating light beam to scan the entire surface of the wafer. To perform the above-described short scan path segment scans, the time required to scan the entire surface depends on a number of factors. One factor obviously is the angle of illumination of the illuminating beam, or the value of θ, that is the angle between the illuminating beam and normal 150 to surface 40 to be inspected shown in FIG. 3. The larger the value of θ (that is, the smaller the grazing angle of incidence), the more elongated would be the shape of the spot 10 in FIG. 1A, and the larger is the area being inspected. Another factor affecting throughput is the fact that the intensity distribution of the illuminating beam is typically not flat but varies, such as in the form of a Gaussian distribution. Therefore, the intensity of scattering from a location on a surface would depend on the intensity of the illuminating light at that location. In order to compensate for such variation of intensity, a number of data points are obtained from the scattering from the particular location of the surface as the spot is moved across the location in a manner illustrated in FIG. 6 described below.

FIG. 6 is a schematic view of three positions of the illuminated area on a surface to be inspected to illustrate the scanning and data gathering process of system 20. As shown in FIG. 6, at one instant in time, beam 38 illuminates an area 10 on surface 40. Area or spot 10 is divided into sixteen pixels by grid lines x1–x5, y1–y5. In this context, the term "pixel" is meaningful only in reference to the taking of data samples across the intensity distribution such as that in FIG. 1B and subsequent data processing and is borrowed from data sampling and processing in other technologies such as video technology. The pixel that is bounded by grid lines x2, x3 and y2, y3 is pixel P shown as a shaded area in FIG. 6. If there is an anamoly in this pixel P, and if the light illuminating pixel P has the intensity distribution as shown in Fig. 1B with a high intensity level between grid lines y2 and y3, light scattered by the anamoly would also have a high intensity. However, as the beam moves along the Y axis so that the area 10' is illuminated instead, pixel P is still illuminated but at a lower intensity level of that between grid lines y1 and y2; in reference to FIG. 1B, the intensity of the illumination is that between grid lines yl and y2 in Fig. lB. Therefore, if the sampling rate employed by the processor 200 in FIG. 3 for processing light detected by the collection or collector channels 110a, 110b, 111a, 111b is such that a sample is taken when the illuminating beam is in position 10 and when the illuminating beam is in position 10', then two data points will be recorded. Thus if pixel P contains an anamoly, then two data points will be taken, one when the illumination is at a higher level as illustrated by data point D2 in Fig. 1B and another one when the illumination is at a lower level, illustrated at data point D1 in FIG. 1B. If position 10 is not the starting position in the short scan path segment 50 illustrated in FIGS. 3 and 4, then two prior samples would have been taken prior to the time when the illuminating beam illuminates the surface 40 in position 10, so that the processor would have obtained two more data points D3, D4 corresponding to the prior positions of the illuminating beam when light of intensity values between grid lines y3, y4 and between y4, y5 respectively illuminates such pixel P. In other words, four separate data points D1–D4 would have been taken of the light scattered by the anamoly in pixel P as the illumination beam illuminates pixel P when scanning along the Y direction.

In most laser beams, the beam intensity has a Gaussian distribution not only in the Y direction but also in the X direction. For this reason, after the illuminating beam completes the scanning operation for scanning a short scan path segment such as segment 50 as shown in FIG. 4, and when the illuminating beam returns to position 74 for scanning the adjacent short scan path segment 50', it is desirable for the illuminated area along path 50' to overlap that of scan path 50 so that multiple samples or data points can again be taken also along the X direction as well as along the Y direction. Spot 10 is not drawn to scale in FIG. 4 to show overlap between adjacent scan segments. Therefore, when the illumination beam is scanning along scan line 50' from starting position 74 as shown in FIG. 4, the area illuminated would overlap spot 10; this overlapping spot is 10" as shown in FIG. 6, where the spot 10" is displaced along the negative X direction relative to spot 10 by one quarter of the long axis of the ellipse 10 and 10".

As described above, the minimum width (that is, length of short axis) of the spots 10, 10', 10" is w. If the angle between the illuminating light beam and normal 150 to the surface 40 to be inspected is θ as shown in FIG. 3, then the magnitude of the long axis of the ellipse 10, 10', 10" is w/cosθ. Therefore, in each short scan path segment, the area illuminated sequentially by the illuminating light beam is given by (w/cosθ)*1, where 1 is the length of the scan path segment such as 50. Thus if the radius of surface 40 is R and T is the time it takes for the beam to scan the short scan path segment, then the time it takes for the illuminating beam to scan across the entire wafer is given by Nπ R²Tcosθ/1w (where the duty factor and the time required for illumination optics to move the beam between strips, such as strips 54, 56 have not been accounted for). In this expression, N is the number of pixels along the X axis in each spot such as 10, 10', 10", since each pixel on the surface will be illuminated N number of times during the scanning process to account for the variation of intensity of illumination in the X direction as described above. In the preferred embodiment illustrated in FIG. 6, where four data points are taken in both the X and Y directions, N has the value 4.

In the scanning process described above in reference to FIGS. 2–4, it is noted that it will require time for the illumination optics to move the illumination spot between strips, such as strips 54 and 56. If τ is the time required to move the illumination spot between strips, then this additional time should be accounted for to give the total time required to scan the entire wafer surface. In the preferred embodiment described above, a stage 124 which includes a motor is used in order to move the surface so as to move the illumination spot from the position for scanning one strip on the surface to the adjacent strip as shown in FIGS. 2 and 3. For a circular wafer of radius R, the spot will need to be moved 2R/η1 times between adjacent strips to move the spot across all the strips on the entire wafer, so that the additional time required is 2Rτ/η1, where η is the duty factor (explained below).

As known to those skilled in the art, when AOD 30 is used to cause beam 38 to scan along each short scan path segment such as 50, time will be required at the beginning of the scan for the sound waves generated by the transducer portion of the AOD to reach the far end of the AOD crystal so as to begin deflecting the beam. This is accounted for by a quantity called the duty factor η given by equation 2 below, and therfore, the total $t_s$ it takes system 20 to scan the entire surface of a wafer with radius R is given by equation 3 below:

$$\eta = 1 - \frac{4kl}{\pi w T \Delta f} \quad (2)$$

$$t_s = \frac{N\pi R^2 T \cos\theta + 2R\tau w}{\eta l w} \quad (3)$$

From equation 3 above, it is evident that the shorter the time T to scan along a scan path segment such as 50, the shorter will be the time required to scan the entire wafer and therefore the higher the throughput. The time T is referred to as the chirp duration which also determines the data rate. The speed of the electronic circuit for processing the data ultimately sets a lower limit for the chirp duration.

From equation 1 above, for a given spot size, length of the scan path segment and the value of k, it is evident that the larger the bandwidth Δf or f2–f1, the smaller will be the clear aperture required of the AOD. To get maximum bandwidth from the AOD, the AOD should be operated at the highest possible frequency and one then expects to get one octave bandwidth around the center frequency of the transducer. However, the acoustic losses in the AOD crystal increase with the center frequency of operation. Large acoustic losses can cause two major problems: reduction in diffraction efficiency and thermal errors induced in the crystal. A reduction in the diffraction efficiency reduces the sensitivity of the system to small particles. When the AOD transducer is operated at high frequencies, more of the acoustic energy will be converted into heat which sets up thermal gradients in the AOD crystal. Such thermal gradients would cause errors by degrading the focal spot which in turn leads to a reduction in sensitivity for detecting anamolies. It is therefore advantageous to minimize the acoustic losses by selecting as low a center frequency of the transducer as possible. A compromise should then be found to yield acceptable detection sensitivity as well as acceptable throughput. Applicants found that a center frequency in the range of 50–300 megahertz and a bandwidth preferably within the range of 50–250 megahertz would be acceptable. The AOD 30 is preferably driven by a linear frequency modulated (FM) chirp signal from generator 80 in FIG. 2. The quantity η1 is the effective length of the scan path segment; in the preferred embodiment the effective length is in the range of 2 to 10 mm but more preferably has a value of about 5.47 mm, where 1 has the value of 6.2 mm.

From equation 3 above, it is seen that the larger the angle θ, the higher will be the throughput, since the illuminated spot will cover a larger area of the surface. But as noted above, the larger the spot size, the lower will be the sensitivity of detection. In the preferred embodiment, θ is in the range of 10°–85° and more preferably in the range of 50°–80°.

Also from equation 3 above, it is evident that the larger the number of samples taken across the illuminated spot diameter, the more time it would take to scan the wafer. In the preferred embodiment, the number of samples taken across the illuminated spot diameter along both orthogoanl axes (X, Y) is in the range of 2–10. Where four samples are taken along at least the x axis, N is 4 in equation 3.

For sensitivity considerations, it is preferable for the minimum width w of the illuminated area to be in the range of 5–15 microns. If θ is in the range of 50°–80°, then the illuminating beam will illuminate the scan path segments such as 50 at such speed that the surface is inspected at a speed not less than about 2.5 cm$^2$/s, and more preferably in a range of about 2.5–3.8 cm$^2$/s.

From equation 3 above, if the time required for moving the wafer or the illumination beam so that the illuminated spot is transferred between adjacent strips such as strips 54, 56 is taken into account, then the average speed for scanning the entire surface 40 will be reduced compared to that for scanning a short scan path segment such as segment 50. Furthermore, the speed for inspecting the entire wafer is further reduced because each pixel on the wafer is scanned multiple times as described above in reference to FIG. 6. If the value of τ is about 0.3 seconds, and where the scan speed along each scan path segment is not less than 2.5 cm$^2$/s, then the average speed for the illumination beam scanning the entire surface is not less than about 1.5 cm$^2$/s. In the preferred embodiment, the average speed is preferably within the range of about 1.55–5 cm$^2$/s. If the surface 40 scanned has dimensions of not less than 200 millimeters in any direction along the surface, then the illumination beam will scan the entire surface in about 50–90 seconds. As noted above, the length of the scan path segments such as segment 50 is preferably small compared to the dimensions of the surface 40 inspected. In the preferred embodiment, these segments are substantially in the range of about 2–10 millimeters.

In the preferred embodiment, generator 80 supplies a linear FM chirp signal to drive the AOD so that the chirp duration is preferably in the range of 20–200 microseconds, and more preferably in the range of about 80–120 microseconds. The beam 28 before deflection by the AOD 30 has at least one cross-sectional dimension (e.g. the longer dimension) in the range of about 4–12 millimeters. Preferably, the scan lens 36 is placed substantially at one focal length away from AOD 30 so that beam 38 scans the surface 40 telecentrically.

From the above, it will be evident that the objective of the invention of the high sensitivity and high throughput surface inspection system has been achieved while moderate data rate (e.g. 22 Mhz) at modest cost for the data sampling and processing electronics can still be achieved. This system is capable of inspecting patterned wafers with 0.35 micron design rule, such as patterned wafers for 64 and 256 megabit DRAM technology. The system is capable of detecting contaminant particles and pattern defects on memory and logic devices. With the present state-of-the-art robotic implementation for removing and replacing wafer 40 on stage 124 ready for system 20 to inspect and the inherent delay (about 25 seconds/wafer) involved therein, system 20 described above is capable of inspecting in excess of about 40 wafers per hour for 150 millimeter diameter wafers (6-inch wafers), in excess of about 20 wafers per hour for 200 millimeter diameter wafers (8-inch wafers) and in excess of about 10 wafers per hour for 300 millimeter diameter wafers (12-inch wafers).

FIGS. 7A, 7B are side views showing the polarization schemes employed by the present invention. It is found that by employing certain polarization schemes, the signal-to-background of the system can be substantially improved. The polarization scheme employed may be surface-dependent and may also be used to determine the composition of the anamoly (such as metallic as opposed to dielectric material). For pattern defects, the polarization elements included in the post-AOD and polarization selection optics 34 of FIG. 2 faces the illumination beam in a state of either P or S polarization. FIG. 7A illustrates the situation where the illumination beam 214 is in a state of S polarization where the electrical field E is perpendicular to the plane of incidence which is defined by the incident beam 214 and the speculatory reflected beam 214a; this plane of incidence is parallel to the plane of the paper. A vector representation of the beam is shown by a k vector representing the direction of propagation. The magnetic field is shown as the H vector. The electric field vector is shown as being perpendicular to the plane of incidence by representing it with a dot and labeled E. In FIG. 7B, the beam 214 is in a state of P polarization where the electric field E is in the plane of incidence and the plane of the paper. In FIG. 7B the beam 214 is shown in vector form with a propagation vector k, a magnetic field vector shown as a dot labeled H where the electric field vector E is perpendicular to the propagation vector k. Instead of P or S polarization states, the illumination beam can also have a left or righthanded circular polarization. Where the polarization state of the illumination beam is chosen to optimize signal-to-noise background and for defect detection, the collector or collection channels include polarization filters to pass light of predetermined polarization states to enhance detection capability and signal-to-noise ratio.

While in the invention described above, the scan path segments are described and illustrated as straight lines, it will be understood that it is also possible for curved scan lines to be employed, such as where the wafer is rotated about an axis instead of translated along straight lines in the X and Y directions as described above. While in the preferred embodiment described above, the short scan path segments form arrays, each array covering a substantially rectangular strip of the wafer, it will be understood that other different arrangements of the scan path segments are possible for covering the entire or substantially the entire surface 40; such and other variations are within the scope of the invention. As the spot 10 approaches the edge of surface 40, the length of the scan path segment may be reduced so that the spot does not fall outside surface 40. All the advantages described are obtained even though the segments are of different lengths if each of at least some of the segments has a span shorter than the dimensions of the surface. Also, the AOD 30 may be replaced by a polygonal scanner or galvonometer. While the invention has been described by reference to preferred embodiments, it will be understood that modifications and changes can be made without departing from the scope of the invention which is to be defined only by the appended claims.

What is claimed is:

1. A method for detecting anomalies on a surface; comprising the steps of:

directing a focused beam of light at a grazing angle towards said surface;

causing relative motion between the beam and the surface so that the beam scans a scan path covering substantially the entire surface, said path including a plurality of arrays of scan path segments, wherein each of at least some of such scan path segments has a span shorter than the dimensions of the surface; and collecting light scattered along said path for detecting anomalies.

2. The method of claim 1, wherein said directing step directs said beam to illuminate an area of the surface defining a spot having a spot size whose minimum width is in the range of about 5 to 15 microns.

3. The method of claim 2, said surface being that of a semiconductor wafer, wherein the spot size and said directing and causing steps are such that the beam substantially inspects the entire surface of the wafer at a throughput in excess of about 40 wafers per hour for 150 mm diameter wafers, at a throughput in excess of about 20 wafers per hour for 200 mm diameter wafers, and at a throughput in excess of about 10 wafers per hour for 300 mm diameter wafers.

4. The method of claim 2, wherein the scan path segments comprise a plurality of straight scan path segments, wherein said directing and causing steps are such that the beam substantially inspects said surface along said scan path segments at such speed that the surface is inspected along said scan path segments at a speed not less than about 2.5 $cm^2/s$.

5. The method of claim 4, wherein the spot size and said directing and causing steps are such that the beam substantially inspects said surface along said scan path segments at such speed that the surface is inspected along said scan path segments at a speed in a range of about 2.5 to 3.8 $cm^2/s$.

6. The method of claim 2, wherein the spot size and said directing and causing steps are such that the beam substantially inspects said surface at such speed that the surface is inspected at a speed not less than about 1.5 $cm^2/s$.

7. The method of claim 6, wherein the spot size and said directing and causing steps are such that the beam substantially inspects said surface at such speed that the surface is inspected at a speed in the range of about 1.5 to 5 $cm^2/s$.

8. The method of claim 2, said surface having dimensions of not less than 200 mm in any direction along the surface, wherein the spot size and said directing and causing steps are such that the beam scans substantially the entire surface in about 50 to 90 seconds.

9. The method of claim 2, said method employing an acousto-optic deflector for deflecting the light beam in order to scan said surface, said method further comprising expanding the optical beam before it is deflected by the deflector, so that the beam before deflection has at least one cross-sectional dimension in the range of about 4 to 12 mm.

10. The method of claim 1, wherein the scan path segments comprise a plurality of arrays of substantially parallel and straight scan path segments, wherein the segments are substantially in a range of about 2–10 mm long.

11. The method of claim 1, wherein said directing step directs said beam to illuminate an area of the surface defining a spot, said beam having an intensity distribution in reference to two axes across the spot, said method further comprising taking a number of samples of the light scattered from any anomaly, if any, in the spot along each of the two axes, said number being in the range of 2 to 10.

12. The method of claim 1, wherein said directing step is such that the angle between the beam and normal direction to the surface is in the range of about 10 to 85 degrees.

13. The method of claim 12, wherein said directing step is such that the angle between the beam and normal direction to the surface is in the range of about 50 to 80 degrees.

14. The method of claim 1, said method employing an acousto-optic deflector for deflecting the light beam in order to scan said surface, said directing and causing steps including driving the deflector with a linear FM chirp signal with a center frequency in the range of 50 to 300 MHz.

15. The method of claim 1, said method employing an acousto-optic deflector for deflecting the light beam in order to scan said surface, said directing and causing steps including driving the deflector with a linear FM chirp signal with a bandwidth in the range of 50 to 250 MHz.

16. The method of claim 15, further comprising supplying a linear FM chirp signal to drive the acousto-optic deflector so that the chirp duration is in the range 20 to 200 microseconds.

17. The method of claim 15, further comprising supplying a linear FM chirp signal to drive the acousto-optic deflector so that the chirp duration is in the range of about 80 to 120 microseconds.

18. The method of claim 1, said method employing an acousto-optic deflector for deflecting the light beam in order to scan said surface, said method further comprising providing a scan lens substantially at one focal length away from the deflector and between the deflector and the surface so that the beam scans the surface telecentrically.

19. The method of claim 1, said method employing a polygon scanner for deflecting the light beam in order to scan said surface, said method further comprising providing a scan lens substantially at one focal length away from the deflector and between the deflector and the surface so that the beam scans the surface telecentrically.

20. The method of claim 1, said collecting step collecting light scattered along said scan path in the forward direction azimuthally.

21. The method of claim 20, said collecting step collecting light scattered along said scan path using four independent collection channels, two of said collection channels located in the forward direction to collect light in the forward direction substantially at ±45° azimuthally and two of the channels are located to collect light substantially at ±90° azimuthally.

22. The method of claim 21, each of said collection channels collects light in the range of 3 to 30° in the elevation direction, said channels collecting light in the respective ranges of azimuthal angles of $-(75-105)°$, $(75-105)°$, $-(30-60)°$ and $(30-60)°$.

23. The method of claim 1, said method further comprising selecting a desired polarization state of a light beam that is directed in the directing step from S state, P state, or a circular polarization state.

24. A system for detecting anomalies on a surface; comprising:

means for directing a focused beam of light at a grazing angle towards said surface;

means for causing relative motion between the beam and the surface so that the beam scans a scan path covering substantially the entire surface, said path including a plurality of arrays of scan path segments, wherein each of at least some of such scan path segments has a span shorter than the dimensions of the surface; and means for collecting light scattered along said path for detecting anomalies.

25. The system of claim 24, wherein said directing means directs said beam to illuminate an area of the surface defining a spot having a spot size whose minimum width is in the range of about 5 to 15 microns.

26. The system of claim 25, said surface being that of a semiconductor wafer, wherein the spot size and said directing and causing means are such that the beam substantially inspects the entire surface of the wafer at a throughput in excess of about 40 wafers per hour for 150 mm diameter wafers, at a throughput in excess of about 20 wafers per hour for 200 mm diameter wafers, and at a throughput in excess of about 10 wafers per hour for 300 mm diameter wafers.

27. The system of claim 25, wherein the scan path segments comprise a plurality of straight scan path segments, wherein the spot size and said directing and causing means are such that the beam substantially inspects said surface along said scan path segments at such speed that the surface is inspected along said scan path segments at a speed not less than about 2.5 $cm^2$/s.

28. The system of claim 27, wherein the spot size and said directing and causing means are such that the beam substantially inspects said surface along said scan path segments at such speed that the surface is inspected along said scan path segments at a speed in a range of about 2.5 to 3.8 $cm^2$/s.

29. The system of claim 25, wherein the spot size and said directing and causing means are such that the beam substantially inspects said surface at such speed that the surface is inspected at a speed not less than about 1.5 $cm^2$/s.

30. The system of claim 29, wherein the spot size and said directing and causing means are such that the beam substantially inspects said surface at such speed that the surface is inspected at a speed in the range of about 1.5 to 5 $cm^2$/s.

31. The system of claim 25, said surface having dimensions of not less than 200 mm in any direction along the surface, wherein the spot size and said directing and causing means are such that the beam scans substantially the entire surface in about 50 to 90 seconds.

32. The system of claim 25, said system employing an acousto-optic deflector for deflecting the light beam in order to scan said surface, said system further comprising expanding the optical beam before it is deflected by the deflector, so that the beam before deflection has at least one cross-sectional dimension in the range of about 4 to 12 mm.

33. The system of claim 24, wherein the scan path segments comprise a plurality of arrays of substantially parallel and straight scan path segments, wherein the segments are substantially in a range of about 2–10 mm long.

34. The system of claim 24, wherein said directing means directs said beam to illuminate an area of the surface defining a spot, said beam having an intensity distribution in reference to two axes across the spot, said system further comprising taking a number of samples of the light scattered from any anomaly, if any, in the spot along each of the two axes, said number being in the range of 2 to 10.

35. The system of claim 24, wherein said directing means is such that the angle between the beam and normal direction to the surface is in the range of about 10° to 85°.

36. The system of claim 35, wherein said directing means is such that the angle between the beam and normal direction to the surface is in the range of about 50° to 80°.

37. The system of claim 24, said system employing an acousto-optic deflector for deflecting the light beam in order to scan said surface, said directing and causing means including driving the deflector with a linear FM chirp signal with a center frequency in the range of 50 to 300 MHz.

38. The system of claim 24, said system employing an acousto-optic deflector for deflecting the light beam in order to scan said surface, said directing and causing means including driving the deflector with a linear FM chirp signal with a bandwidth in the range of 50 to 250 MHz.

39. The system of claim 38, further comprising means for supplying a linear FM chirp signal to drive the acousto-optic deflector so that the chirp duration is in the range 20 to 200 microseconds.

40. The system of claim 38, further comprising means for supplying a linear FM chirp signal to drive the acousto-optic deflector so that the chirp duration is in the range of about 80 to 120 microseconds.

41. The system of claim 24, said system employing an acousto-optic deflector for deflecting the light beam in order to scan said surface, said system further comprising a scan lens substantially at one focal length away from the deflector and between the deflector and the surface so that the beam scans the surface telecentrically.

42. The system of claim 24, said system further comprising:

a polygon scanner for deflecting the light beam in order to scan said surface; and a scan lens substantially at one focal length away from the deflector and between the deflector and the surface so that the beam scans the surface telecentrically.

43. The system of claim 24, said collecting means collecting light scattered along said scan path in the forward direction azimuthally.

44. The system of claim 43, said collecting means comprising four independent collection channels collecting light scattered along said scan path, two of said collection channels located in the forward direction to collect light in the forward direction substantially at ±45° azimuthally and two of the channels are located to collect light substantially at ±90° azimuthally.

45. The system of claim 44, each of said collection channels collects light in the range of 3° to 30° in the elevation direction, said channels collecting light in the respective ranges of azimuthal angles of −(75–105)°, (75–105)°, −(30–60)° and (30–60)°.

46. The system of claim 24, said system further comprising selecting a desired polarization state of a light beam that is directed in the directing means from S state, P state, or a circular polarization state.

* * * * *